United States Patent
Sendatzki et al.

(10) Patent No.: US 9,566,394 B2
(45) Date of Patent: Feb. 14, 2017

(54) DRIVE MECHANISM FOR A DRUG INJECTION DEVICE COMPRISING ADHESIVE TO BLOCK DRIVE AT END OF DEVICE LIFE TO PREVENT REUSE

(71) Applicant: SANOFI-AVENTIS DEUTSCHLAND GMBH, Frankfurt am Main (DE)

(72) Inventors: Günther Sendatzki, Frankfurt am Main (DE); Michael Jugl, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 166 days.

(21) Appl. No.: 14/388,556

(22) PCT Filed: Apr. 2, 2013

(86) PCT No.: PCT/EP2013/056851
§ 371 (c)(1),
(2) Date: Sep. 26, 2014

(87) PCT Pub. No.: WO2013/149978
PCT Pub. Date: Oct. 10, 2013

(65) Prior Publication Data
US 2015/0051544 A1 Feb. 19, 2015

(30) Foreign Application Priority Data
Apr. 5, 2012 (EP) .................... 12163483

(51) Int. Cl.
*A61M 5/50* (2006.01)
*A61M 5/24* (2006.01)
*A61M 5/315* (2006.01)

(52) U.S. Cl.
CPC ............ *A61M 5/50* (2013.01); *A61M 5/24* (2013.01); *A61M 5/31501* (2013.01);
(Continued)

(58) Field of Classification Search
CPC ...... A61M 5/50; A61M 5/24; A61M 5/31501; A61M 5/502; A61M 5/20; A61M 5/315; A61M 5/31576; A61M 5/3159; A61M 5/31591; A61M 5/31583; A61M 2005/31508; A61M 2205/273; A61M 2205/27
See application file for complete search history.

(56) References Cited

U.S. PATENT DOCUMENTS

| | | | | |
|---|---|---|---|---|
| 5,533,970 A | * | 7/1996 | Berger | A61M 5/322 604/110 |
| 2009/0156074 A1 | * | 6/2009 | Lu | C09J 133/08 442/151 |
| 2011/0054412 A1 | * | 3/2011 | Eich | A61M 5/20 604/207 |

FOREIGN PATENT DOCUMENTS

| | | |
|---|---|---|
| CN | 101553265 A | 10/2009 |
| DE | 10239443 | 3/2004 |

(Continued)

OTHER PUBLICATIONS

International Search Report for Int. App. No. PCT/EP2013/056851, completed May 29, 2013.
(Continued)

*Primary Examiner* — Bhisma Mehta
*Assistant Examiner* — Nilay Shah
(74) *Attorney, Agent, or Firm* — McDonnell Boehnen Hulbert & Berghoff LLP

(57) ABSTRACT

A drive mechanism of a drug delivery device is presented having, a piston rod to operably engage with a piston of a cartridge containing a medicament, a first functional component and a second functional component whose position or orientation relative to each other is unambiguously correlated to a predefined axial position of the piston rod, wherein the first and/or the second functional component
(Continued)

comprise at least one engaging portion to inseparably and to adhesively engage the first and the second functional component with each other for rendering the drive mechanism inoperable when the predefined axial position of the piston rod has been reached.

6 Claims, 3 Drawing Sheets

(52) U.S. Cl.
CPC .... *A61M 5/31551* (2013.01); *A61M 5/31585* (2013.01); *A61M 5/502* (2013.01); *A61M 2005/31508* (2013.01); *A61M 2205/27* (2013.01); *A61M 2205/273* (2013.01)

(56) References Cited

FOREIGN PATENT DOCUMENTS

| | | | |
|---|---|---|---|
| DE | 102006038101 | 2/2008 | |
| EP | 0594349 | 4/1994 | |
| EP | 1911480 | 4/2008 | |
| GB | 476959 A | * 12/1937 | ........... B24D 11/005 |
| WO | 2004/078241 | 9/2004 | |

OTHER PUBLICATIONS

International Preliminary Report on Patentability for PCT Application No. PCT/EP2013/056851, issued Oct. 7, 2014.
Written Opinion for PCT Application No. PCT/EP2013/056851, dated Oct. 5, 2014.

* cited by examiner

DRIVE MECHANISM FOR A DRUG INJECTION DEVICE COMPRISING ADHESIVE TO BLOCK DRIVE AT END OF DEVICE LIFE TO PREVENT REUSE

CROSS REFERENCE TO RELATED APPLICATIONS

The present application is a U.S. National Phase Application pursuant to 35 U.S.C. §371 of International Application No. PCT/EP2013/056851 filed Apr. 2, 2013, which claims priority to European Patent Application No. 12163483.6 filed Apr. 5, 2012. The entire disclosure contents of these applications are herewith incorporated by reference into the present application.

TECHNICAL FIELD

The present invention relates to drive mechanism for a drug delivery device, such as a pen-type injector and in particular to drug delivery devices of disposable type intended to be completely discarded once the medicament provided therein has been used up.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing adapted to receive a cartridge at least partially filled with the medicament to be dispensed. The device further comprises a drive mechanism, typically having a displaceable piston rod which is adapted to operably engage with a piston of the cartridge. By means of the drive mechanism and its piston rod, the piston of the cartridge can be displaced in a distal or dispensing direction and may therefore expel a predefined amount of the medicament via a piercing assembly which is to be releasably coupled with a distal end section of the housing of the drug delivery device.

Among different types of pen injectors there exist disposable drug delivery devices which are intended to be discarded in their entirety once the medicament provided in the cartridge is used up. With these devices, empty cartridges are not to be replaced. Instead, a new drug delivery device with a filled cartridge readily arranged therein should be purchased and applied by the patient or user.

Disposable drug delivery devices may be frequently subject to misuse, in particular in combination with counterfeited medicaments. Hence, original drug delivery devices may be disassembled and an empty cartridge may be replaced by a filled one while resetting the drive mechanism intended to interact with the cartridge.

Such illegitimate manipulation of a drug delivery device implicits an undue risk of health of the patient using such a device.

It is therefore an object of the present invention to provide an anti-counterfeiting means to inhibit illegitimate manipulation of disposable drug delivery devices after their intended use. The anti-counterfeiting means should be implementable into existing drug delivery devices as smooth and easy as possible and should come along with negligible cost- and implementation efforts.

SUMMARY

In a first aspect, the invention provides a drive mechanism of a drug delivery device comprising a piston rod, which is adapted to operably engage with a piston of a cartridge. The cartridge contains a medicament to be dispensed by way of a distally directed displacement of the piston relative to the cartridge of e.g. tubular shape. The drive mechanism comprises a first and a second functional component, which, when in use, exhibit a position or an orientation relative to each other that is unambiguously correlated to a predefined axial position of the piston rod. Said predefined axial position may be determined relative to a housing of the drug delivery device.

Since the piston rod typically engages with a piston of a cartridge, said predefined axial position of the piston rod may also be correlated with the position of the piston and/or may be governed by a corresponding predefined position of the piston relative to the cartridge. Hence, the relative position or orientation of the first and second functional components is indicative of the filling level of the cartridge when the drive mechanism and the cartridge are operably engaged during operation of the drug delivery device. Typically, the predefined axial position of the piston rod and/or of the piston is represents a last dose position indicating that the cartridge is almost empty.

The first and/or the second functional components further comprise at least one engaging portion to inseparably engage the first and the second functional component with each other when the predefined axial position of the piston rod and/or when a corresponding predefined axial position of the piston relative to the cartridge has been reached. It is particularly intended that the first and the second functional components mutually engage when the piston rod reaches an axial position that corresponds to a substantially empty cartridge. Consequently, when the drive mechanism comprises a piston rod to operably engage with the piston of the cartridge, mutual engagement of first and second components may also be governed by a predefined axial position of the piston relative to the cartridge.

Moreover, by inseparably engaging first and second functional components said components may no longer be moveable with respect to each other thereby rendering the drive mechanism substantially inoperable. First and second functional components are selected such, that operation of the drive mechanism, e.g. a dose setting and/or a dose dispensing action comes along with a relative displacement or movement of first and second functional components. By mutually engaging and mutually fixing first and second functional components by means of the at least one engaging portion, a further operation of the drive mechanism is effectively disabled. Since first and second functional components are to be inseparably engaged by the at least one engaging portion, the drive mechanism may not be resurrected or reset once it has been rendered inoperable.

This way, once a predefined axial position of the piston and once a corresponding pre-defined end configuration of the drive mechanism has been reached, the drive mechanism becomes inoperable and may not become subject to a reset procedure. In effect, even the device would be disassembled for an illegitimate replacement of a cartridge, the drive mechanism cannot be reset and the entire drug delivery device is of no further use.

The engaging portion may be provided with the first and/or with the second functional component and is intended to engage or to mechanically interconnect the two components once the engaging portion of e.g. the first functional component gets either in direct contact with the second functional component or with a corresponding engaging portion of the second functional component. The at least one engaging portion may be provided as a separate piece or member to be attached to the first and/or to the second functional component. It may also be provided on or as a contact surface of the first and/or of the second functional component. Hence, the engaging portion may be integrally formed with the first and/or with the second functional component.

The above-mentioned concept of rendering a drive mechanism inoperable is generally applicable to a manifold of different drive mechanisms and drug delivery devices. In general and depending on the type of drive mechanism, various components thereof may serve as first and second functional components as long as their relative distance or orientation with respect to each other is somehow correlated or indicative of the axial position of the piston in the cartridge which is to be displaced by means of the drive mechanism.

The first and the second functional components and the at least one engaging portion are designed such that the two functional components inseparably engage when the drive mechanism reaches an end configuration, that is a configuration in which the piston rod reaches a distal end position typically corresponding with the piston of the cartridge reaching a distal end position within an emptied cartridge.

In the present context the distal direction corresponds with the injection direction and points towards a dispensing end of the drug delivery device whereas the opposite, proximal direction faces away from the patient and from the dispensing end of the drug delivery device. Typically, the drug delivery device features some kind of dose setting or dose dispensing means at its proximal end.

The engaging portion of first and/or second functional components is further adapted to adhesively engage the first and the second functional components once these components get in direct mechanical contact. By adhesively engaging or bonding together first and second functional components, the components are effectively hindered to move relative to each other, thereby effectively blocking any further operation of the drive mechanism.

Additionally or alternatively, the engaging portion may be further adapted to frictionally engage the first and the second functional components once a pre-defined configuration of the drive mechanism has been reached. The frictional engagement between first and second functional components should be such that the drive mechanism gets rather stiff and sluggish, so that a reasonable operation thereof is no longer available.

In a further preferred embodiment it is even conceivable, that the engaging portion is also adapted to positively engage the first and the second functional components. In this embodiment, first and second functional components preferably comprise mutually corresponding positively engaging members by way of which an inseparable engagement of first and second functional components can be established once the mutually corresponding engaging portions interengage.

Irrespective whether inoperability of the drive mechanism is established by an adhesive engagement of first and second functional components it is of particular benefit, that once an inseparable engagement of first and second functional components has been established, these components cannot be released in a non-destructive way.

In a further preferred embodiment, the first functional component comprises a piston rod which is adapted to exert distally directed thrust to the piston of the cartridge. The piston rod as first functional component is particularly adapted to interact with an insert or radially inwardly directed flange of a housing of the drive mechanism or of the drug delivery device, respectively, wherein the insert has a through opening through which the piston rod extends. Hence, the piston rod of the drive mechanism is axially and radially supported by the insert.

Here, the axial position of the piston rod relative to the insert is indicative of the axial position of the piston relative to a tubular shaped barrel of the cartridge. Since the insert may be rigidly connected to a housing of the drive mechanism and since the cartridge may also be fixed with respect to the housing, the axial position of the piston rod relative to the insert is directly indicative of the axial position of the piston inside the cartridge which correlates to the filling level of the cartridge.

It is of particular benefit and according to a preferred embodiment, when the engaging portion is arranged at a proximal end of the piston rod. The axial position of the engaging portion is selected such, that the engaging portion engages with the insert when the piston rod reaches an end configuration, which correlates with a maximum distal displacement of the piston rod. Then, the piston rod mechanically engages with the insert and is effectively immobilized so that the entire drive mechanism is substantially rendered inoperable. In an initial configuration of the drive mechanism, the proximal end of the piston rod is located at an axial distance from the insert and approaches the insert during successive dose dispensing procedures either continuously or stepwise. Hence the proximal end of the piston rod faces or points in a direction opposite to the distally oriented dispensing direction of the drive mechanism.

Axial position and configuration of the engaging portion at or near the proximal end of the piston rod is selected such, that a mutual engagement of insert and piston rod is attained when a final or last dose is dispensed by the drive mechanism.

In a further preferred embodiment, the insert through which the piston rod extends comprises an inner thread which engages with an outer thread of the piston rod. In effect, piston rod and insert are threadedly engaged so that a distally directed displacement of the piston rod relative to the insert is accompanied by a rotative movement thereof. When the last dose configuration is reached in which the engaging portion at the proximal end of the piston rod engages with the inner thread of the insert, any further rotation of the piston rod relative to the insert is effectively blocked and since insert and piston rod are threadedly engaged, a proximally but also a distally directed axial displacement of the piston rod can be effectively impeded.

Alternatively, piston rod and insert do not necessarily have to be threadedly engaged. It is also conceivable, that the piston rod comprises a circumferential structure that matches with an inner structure of the insert's through opening. In such embodiments, relative displacement of piston rod and insert may be non-rotational but purely translational.

In a further preferred embodiment, the engaging portion comprises a pressure sensitive adhesive, which preferably activates when the engaging portion of e.g. the piston rod mechanically engages with the through opening of the insert. As long as the pressure sensitive adhesive is not squeezed between the first and second functional components it is rather inactive but exhibits a respective adhesion or bonding effect on the first and second functional components as soon as it is subject to mechanical impact or pressure, preferably when squeezed between first and second, functional components.

It is of further benefit, when the engaging portion comprises adhesive microspheres adapted to rupture when the engaging portion of the first and/or of the second functional component gets in mechanical contact with the second and/or with the first functional component. Typically, such microspheres are tiny particles featuring a diameter in the submillimeter range. The microspheres may comprise a diameter between 10 and 250 µm and are particularly intended to become subject to rupture and to release an adhesive component encapsulated therein.

By releasing the adhesive, an inseparable mutual engagement of the first and the second functional components of the drive mechanism can be established. Upon release from cracked microspheres the adhesive may start to cure.

Instead of microspheres, the engaging portion of the first and/or of the second functional components may be provided with a rather conventional adhesive comprising a rather greasy constitution. When provided at a proximal end of a piston rod, such a greasing adhesive may contaminate the threaded through opening of the insert thereby notably increasing friction forces between insert and piston rod, so that a further operation of the drive mechanism is no longer given. Moreover, also an adhesive requiring a respective time interval to cure may provide such a contaminating effect on the inner thread of the through opening.

In a further preferred embodiment, the engaging portion comprises a lacquer containing rupturing adhesive microspheres. This way, application of the rupturing adhesive microspheres to the first or second functional component can be provided by simply coating a respective portion of first and/or second functional components with a respective microsphere-containing lacquer. By applying a microsphere-containing lacquer to at least one selected functional component of the drive mechanism, the anti-counterfeiting means according to the present invention can be implemented in a rather simple and cost-efficient way without geometrically modifying any other component of the drive mechanism.

According to another preferred embodiment, the first and second functional components are not provided by a piston rod guided in an insert. Instead, the first functional component comprises a nut threadedly engaged with the second functional component comprising a drive sleeve, wherein the nut is axially slidably engaged with a housing of the drug delivery device and is further rotationally locked to said housing. In this context, the housing may also belong to the drive mechanism since it is functionally coupled to at least the first functional component. The nut is further adapted to axially and/or tangentially but against a flange portion of the drive sleeve when the predefined axial position of the piston rod has been reached. The nut serves as a kind of last dose nut and is originally intended to inhibit to set a dose that exceeds the remaining filling level of the cartridge. Hence, the axial position of the nut relative to the drive sleeve of the drive mechanism is directly indicative of the axial position of the piston rod and hence of the axial position of the piston relative to the cartridge.

The drive sleeve itself or its flange portion may abut with the nut in axial but also in tangential or radial direction. The drive sleeve may comprise a radially extending last dose stop to interact with the nut in tangential or circumferential direction. In this way, mutual displacement, in particular a mutual and relative rotation of the nut and the drive sleeve can be precisely stopped and interrupted when a predefined rotational configuration of the nut and drive sleeve has been reached.

In this embodiment, the drive sleeve rotates with respect to the housing during a dose setting procedure which induces a relative axial displacement of the nut relative to the drive sleeve. Since the nut is rotationally locked to the housing, it inhibits any further rotational and hence dose setting movement of the drive sleeve once the nut abuts against the radially extending flange portion of the drive sleeve.

Here it is of particular benefit, when the nut and/or the flange portion comprise the engaging portion to inseparably engage the nut and the flange portion when getting in mutual contact or in abutment configuration. Once the nut and the flange portion of the drive sleeve inseparably engage, any further rotational movement of the drive sleeve is effectively blocked and inhibited so that neither a reset nor a further dose setting of the drive mechanism is available.

In a further independent aspect, the invention also relates to a drug delivery device for dispensing of a dose of a medicament. The device comprises a housing having a drive mechanism as described above and further has a cartridge holder interconnected with the housing. Furthermore, the drug delivery device comprises a cartridge being at least partially filled with a medicament and being arranged in the cartridge holder. Preferably, said drug delivery device is of disposable type, wherein the cartridge disposed therein is not intended to be replaced when its content is used up.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described by making reference to the drawings, in which.

DETAILED DESCRIPTION

Figure 1:
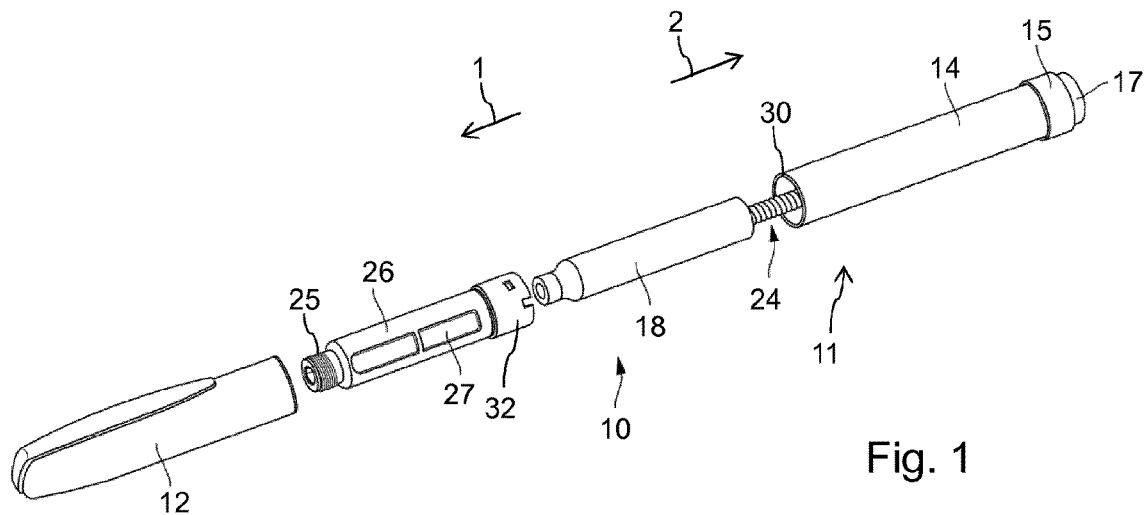
FIG. 1 schematically illustrates a perspective exploded view of a pen-type injector.

The drug delivery device 10 as illustrated in an exploded view in FIG. 1 comprises a proximal or main housing 14 to accommodate a drive mechanism 11. The drive mechanism 11 inter alia comprises a threaded piston rod 24 which is adapted to operably engage with a piston 20 of a cartridge 18 as illustrated in the cross-sectional view according to FIG. 2. The drive mechanism 11 further comprises a dose dial 15 and a dose button 17 at its proximal end by way of which a dose of the medicament can be set and dispensed, respectively.

Figure 2:
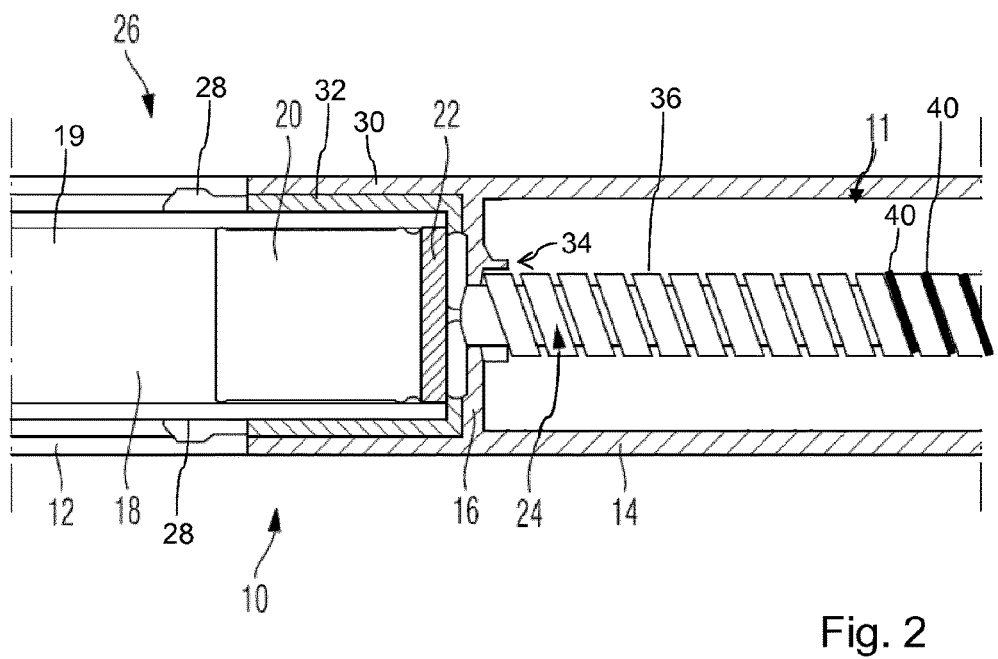
FIG. 2 shows a cross section through a typical pen-type injector having a piston rod with an engaging portion, FIG. 3 schematically illustrates a partial cross section through another drive mechanism of a drug delivery device in an initial configuration.

In distal direction 1, the housing 14 comprises a receptacle 30 adapted to receive an insert portion 32 of a cartridge holder 26. The cartridge holder 26 featuring an inspection window 27 allowing to visually control the filling level of the vitreous cartridge 18 is connected with the housing 14 in an interleaved or nested configuration as shown in FIG. 2. The cartridge holder 26 further comprises radially protruding portions 28 by way of which a protective cap 12 can be releasably mounted on the cartridge holder 26. At its distal or dispensing end, the cartridge holder 26 comprises a threaded socket 25 which is adapted to removably receive a correspondingly threaded needle hub having a double tipped needle to penetrate a distal septum of the cartridge 18 for injecting a dose of the medicament 19, e.g. into biological tissue.

As illustrated in the cross section according to FIG. 2, the proximal housing 14 comprises a radially inwardly protruding flange-like insert 16 featuring a central through opening 34 that engages with the outer thread 36 of the piston rod 24. At its distal end, the piston rod 24 comprises a rotatable pressure piece 22 which is adapted to abut against a proximal end face of the piston 20 and to exert distally directed pressure thereto. A distally directed forward movement of the piston rod 24 may be induced by a rotative movement of the piston rod 24. Due to its threaded engagement with the through opening 34 of the insert 16, the piston rod 24 advances in distal direction 1 when it becomes subject to a rotational movement.

It is particularly intended, that the drug delivery device 10 is of disposable type. In order to provide an anti-counterfeiting means, the piston rod 24 as a first functional component of the drive mechanism 11 is provided with an engaging portion 40 near an end facing in proximal direction 2. The engaging portion 40 may comprise a lacquer containing rupturing adhesive microspheres. As indicated in FIG. 2, the engaging portion 40 is preferably provided in the root of the thread 36 of the piston rod 24. Once the piston rod 24 advances in distal direction 1, also its proximal end shifts towards the insert 16. When a final or last dose configuration of the drive mechanism is reached, in which the piston rod 24 almost completely extends in distal direction 1 through the through opening 34 of the insert 16, the engaging portion 40 gets in direct mechanical contact with the inner thread of the through opening 34. Then, the pressure sensitive adhesive will be released from the ruptured microspheres and will inseparably bond together the piston rod 24 and the insert 16.

Since the insert as the second functional component of the drive mechanism is integrally formed with the housing 14, the piston rod 24 can be substantially bonded and interlocked with the housing 14 once a last dose configuration has been reached. As soon as the engaging portion 40 near a proximal end of the piston rod 24 engages with the threaded through opening 34 of the insert 16, the adhesive is released, thereby also contaminating the inner thread of the through opening 34. Even with a slowly curing adhesive or with a non-curing but rather greasy adhesive, a substantial increase of frictional forces between piston rod 24 and insert 16 can be established which may be sufficient to render the drive mechanism substantially inoperable.

Figure 3:
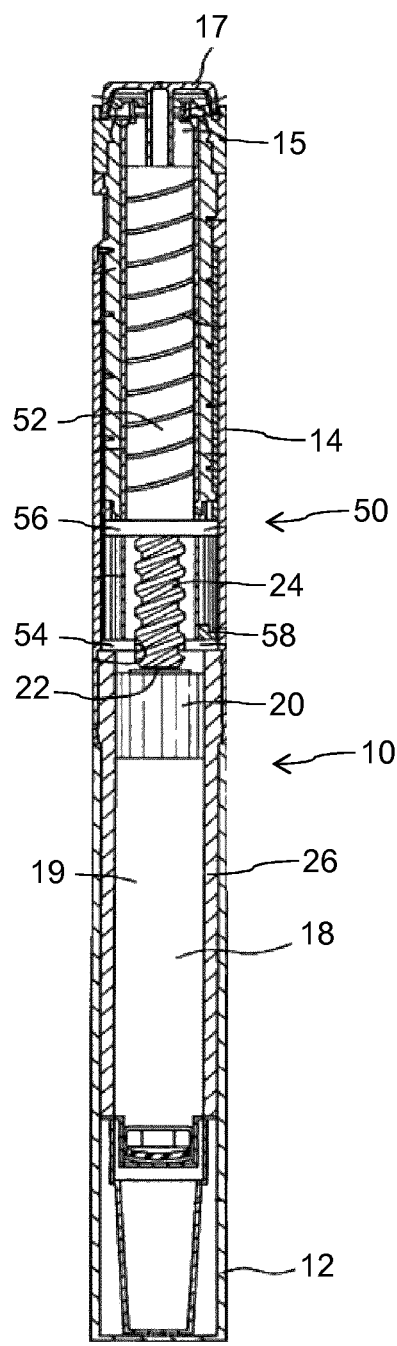
Figure 4:
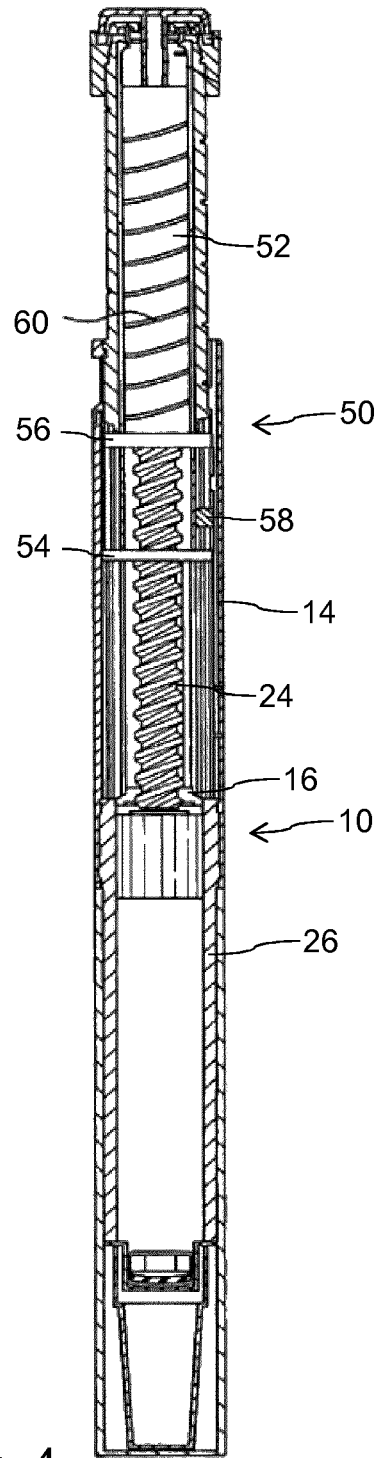
FIG. 4 shows the drive mechanism according to FIG. 3 after setting of a dose and FIG. 5 shows another cross-sectional view of the drive mechanism according to FIGS. 3 and 4.
Figure 5:
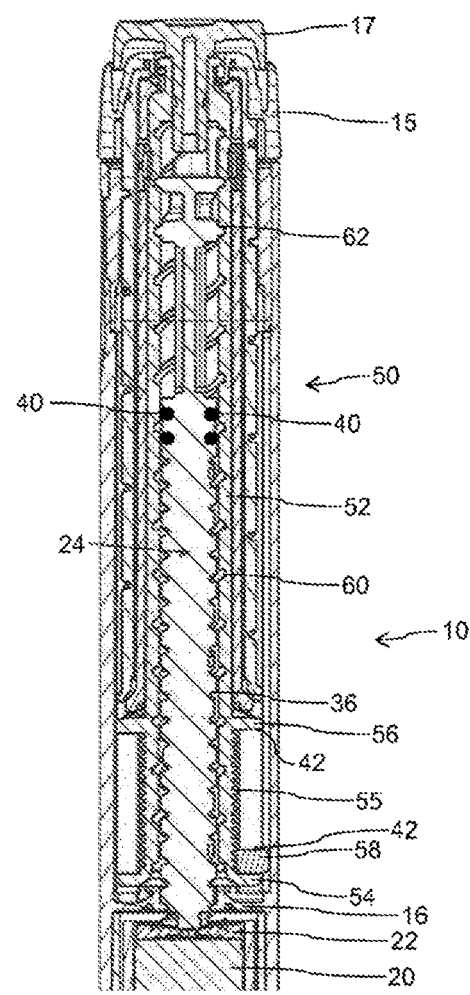

In the various cross-sectional illustrations of FIGS. 3, 4 and 5, another drive mechanism 50 is illustrated providing two different first and second functional components 58, 56 that are applicable to immobilize the drive mechanism and whose relative position is directly correlated with the axial position of the piston 20 inside the cartridge 18.

Generally, identical or similar components already describe in connection with the drug delivery device 10 as shown in FIGS. 1 and 2 are provided with the same reference numerals here.

The drive mechanism 50 as shown in FIGS. 3, 4 and 5 generally resembles the drive mechanism explicitly illustrated and described in WO 2004/078241 A1, which is hereby incorporated by reference. As shown in FIGS. 3 to 5, a generally cylindrical drive sleeve 52 extends about the piston rod 24. This drive sleeve 52 is provided with a first radially extending flange 54 at a distal end and with a second radially extending flange spaced a distance along the drive sleeve 52 from the first flange 54. Between the two flanges 54, 56 an outer thread 55 is provided that mates with a corresponding inner thread of a nut 58.

In radial direction the nut 58 is located between the drive sleeve 52 and the housing 14. The nut 58 is further disposed between the first flange 54 and the second flange 56. The outer surface of the nut 58 and an internal surface of the housing 14 are keyed together by 18 way of splines which are not explicitly illustrated here. By means of this keyed engagement, relative rotation between the nut 58 and the housing 14 is prevented while a relative longitudinal or axial movement of the nut 58 relative to the housing 14 is still allowed.

As shown in FIGS. 3 and 5, where the drive mechanism 50 and its piston rod 24 is in an initial configuration, the nut 58 is located near the first flange 54. By twisting or rotating a dose dial 15 at the proximal end of the drug delivery device, the drive sleeve 52 reaches a proximally extending configuration as illustrated in FIG. 4. As further shown in FIG. 5, the drive sleeve 52 is threadedly engaged with a second, proximally located thread 62 of the piston rod 24 by means of an inner thread 60. The piston 24 further comprises a first thread 36 which is threadedly engaged with the insert 16. Due to the threaded engagement of drive sleeve 52 and piston rod 24 and due to at least one clutch mechanism not further illustrated here, a rotation of the dose dial 15 leads to a screw-like proximally directed displacement of the drive sleeve 52 as illustrated in FIG. 4.

Due to the threaded engagement of nut 58 and drive sleeve 52 and due to the rotational interlock of the nut 58 with regard to the housing 14, a rotational displacement of the drive sleeve comes along with an axial displacement of the nut 58 relative to the drive sleeve 52 as can be seen in FIG. 4. During dose dispensing, the drive sleeve 52 is only subject to a translational and distally directed displacement thereby inducing a rotational movement to the piston rod 24, which in turn experiences a distally directed displacement due to its threaded engagement with the insert 16 of the housing 14.

During a dose dispensing procedure, the relative position of the nut 58 with respect to the drive sleeve 52 and its flange portions 54, 56 will not vary. However, during a subsequent dose setting procedure, the nut 58 will further move towards the second flange 56.

In effect, the axial position of the nut 58 relative to the first flange 54 or to the second flange 56 is directly indicative of the axial position and configuration of the piston rod 24 and hence of the axial position of the piston 20 in the cartridge 18. Once a final dose dispensing configuration is reached, the nut 58 axially abuts with the second flange 56 thereby inhibiting a further rotation of the drive sleeve 52.

Consequently, and in the context of the present invention the nut 58 serves as a first functional component of the drive mechanism 50 whereas the flange 56 acts as the second functional component of the drive mechanism.

It is of particular benefit to provide an engaging portion 42 between the nut 58 and the second flange 56. For instance and as indicated in FIG. 5, a proximal face of the nut 58 may be provided with an engaging portion 42 or with a comparable engaging member which serves to establish an inseparable connection of nut 58 and second flange 56 once a last dose configuration has been reached.

Alternatively or additionally, also the distal face of the flange 56 may be correspondingly provided with an engaging portion 42 or with an engaging member in order to establish an adhesive, frictional or positive engagement between the nut 58 and the flange portion 56 once these two functional components get in direct mutual contact. Also here, the respective surfaces of the nut 58 and the second flange 56 that face towards each other may be coated or applied with a lacquer containing rupturing adhesive microspheres.

Alternatively, also other types of adhesive materials may be applied to the nut 58 and/or to the flange 56. It is also conceivable to equip the nut 58 and the flange 56 with inseparable engaging positive interlock members not particularly illustrated here, by way of which an inseparable mutual engagement of nut 58 and flange 56 can be equally attained.

Once the nut 58 is inseparably attached to the flange 56, neither a clockwise nor a counter-clockwise rotation of the drive sleeve 52 is possible and the drive mechanism 50 is rendered substantially inoperable. It is only optionally, that the piston rod 24 as shown in FIGS. 3-5 comprises a pressure sensitive adhesive 40 near its proximal end.

The invention claimed is:

1. A drive mechanism of a drug delivery device, comprising:
  a piston rod to operably engage with a piston of a cartridge containing a medicament;
  a first functional component; and
  a second functional component,
  where position or orientation of the first functional component and the second functional component relative to each other is unambiguously correlated to a predefined axial position of the piston rod,
  wherein at least one of the first functional component and the second functional component comprises at least one engaging portion to inseparably and to adhesively engage the first functional component and the second functional component with each other for rendering the drive mechanism inoperable when the predefined axial position of the piston rod has been reached,
  wherein the at least one engaging portion comprises a pressure sensitive adhesive, and
  wherein the first functional component comprises the piston rod which is adapted to exert distally directed thrust to the piston of the cartridge, wherein the second functional component comprises an insert having a through opening through which the piston rod extends, wherein the piston rod comprises an outer thread engaged with an inner thread of the through opening, and wherein the at least one engaging portion is arranged at a proximal end of the piston rod.

2. The drive mechanism according to claim 1, wherein the engaging portion comprises adhesive microspheres adapted to rupture when at least one of the engaging portion of the first functional component and the second functional component gets in mechanical contact with the other one of the first functional component and the second functional component.

3. The drive mechanism according to claim 1, wherein the engaging portion comprises a lacquer containing rupturing adhesive microspheres.

4. A drug delivery device for dispensing a dose of a medicament, comprising:
  xa housing,
  a cartridge holder interconnected with the housing, and
  a cartridge at least partially filled with the medicament and being arranged in the cartridge holder, and
  a drive mechanism assembled inside the housing, the drive mechanism comprising:
    a piston rod to operably engage with a piston of the cartridge containing the medicament;
    a first functional component; and
    a second functional component,
    where position or orientation of the first functional component and the second functional component relative to each other is unambiguously correlated to a predefined axial position of the piston rod,
    wherein at least one of the first functional component and the second functional component comprises at least one engaging portion to inseparably and to adhesively engage the first functional component and the second functional component with each other for rendering the drive mechanism inoperable when the predefined axial position of the piston rod has been reached,
    wherein the at least one engaging portion comprises a pressure sensitive adhesive, and
    wherein the first functional component comprises the piston rod which is adapted to exert distally directed thrust to the piston of the cartridge, wherein the second functional component comprises an insert having a through opening through which the piston rod extends, wherein the piston rod comprises an outer thread engaged with an inner thread of the through opening, and wherein the at least one engaging portion is arranged at a proximal end of the piston rod.

5. A drive mechanism of a drug delivery device, comprising:
  a piston rod to operably engage with a piston of a cartridge containing a medicament;
  a first functional component; and
  a second functional component,
  where position or orientation of the first functional component and the second functional component relative to each other is unambiguously correlated to a predefined axial position of the piston rod,
  wherein at least one of the first functional component and the second functional component comprises at least one engaging portion to inseparably and to adhesively engage the first functional component and the second functional component with each other for rendering the drive mechanism inoperable when the predefined axial position of the piston rod has been reached,
  wherein the at least one engaging portion comprises a pressure sensitive adhesive, and
  wherein the first functional component comprises a nut threadedly engaged with the second functional component comprising a drive sleeve, wherein the nut is axially slidably engaged with a housing and rotationally locked to the housing and wherein the nut is further adapted to at least one of axially and tangentially abut against a flange portion of the drive sleeve when the predefined axial position of the piston rod has been reached, and wherein at least one of the nut and the flange portion comprise the at least one engaging portion to inseparably engage the nut and the flange portion when getting in mutual contact.

6. A drug delivery device for dispensing a dose of a medicament, comprising:
  a housing,
  a cartridge holder interconnected with the housing, and
  a cartridge at least partially filled with the medicament and being arranged in the cartridge holder, and
  a drive mechanism assembled inside the housing, the drive mechanism comprising:
    a piston rod to operably engage with a piston of the cartridge containing the medicament;

a first functional component; and
a second functional component,
where position or orientation of the first functional component and the second functional component relative to each other is unambiguously correlated to a predefined axial position of the piston rod,
wherein at least one of the first functional component and the second functional component comprises at least one engaging portion to inseparably and to adhesively engage the first functional component and the second functional component with each other for rendering the drive mechanism inoperable when the predefined axial position of the piston rod has been reached,
wherein the at least one engaging portion comprises a pressure sensitive adhesive, and
wherein the first functional component comprises a nut threadedly engaged with the second functional component comprising a drive sleeve, wherein the nut is axially slidably engaged with a housing and rotationally locked to the housing and wherein the nut is further adapted to at least one of axially and tangentially abut against a flange portion of the drive sleeve when the predefined axial position of the piston rod has been reached, and wherein at least one of the nut and the flange portion comprise the at least one engaging portion to inseparably engage the nut and the flange portion when getting in mutual contact.

* * * * *